United States Patent
Wu et al.

(10) Patent No.: US 11,348,247 B2
(45) Date of Patent: May 31, 2022

(54) SYSTEMS AND METHODS FOR GENERATING SEMANTIC INFORMATION FOR SCANNING IMAGE

(71) Applicant: SHANGHAI UNITED IMAGING HEALTHCARE CO., LTD., Shanghai (CN)

(72) Inventors: Ke Wu, Shanghai (CN); Jieyan Ma, Shanghai (CN); Weijuan Li, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 0 days.

(21) Appl. No.: 16/862,734

(22) Filed: Apr. 30, 2020

(65) Prior Publication Data
US 2020/0258234 A1 Aug. 13, 2020

Related U.S. Application Data

(63) Continuation of application No. PCT/CN2018/113618, filed on Nov. 2, 2018.

(30) Foreign Application Priority Data

Nov. 2, 2017 (CN) .......................... 201711065915.0
Aug. 28, 2018 (CN) .......................... 201810988691.9

(51) Int. Cl.
*G06K 9/00* (2022.01)
*G06T 7/11* (2017.01)
(Continued)

(52) U.S. Cl.
CPC .............. *G06T 7/11* (2017.01); *G06K 9/6256* (2013.01); *G06T 7/12* (2017.01); *G06T 7/149* (2017.01);
(Continued)

(58) Field of Classification Search
CPC ........................................................ G06T 7/11
See application file for complete search history.

(56) References Cited

U.S. PATENT DOCUMENTS 6,263,024 B1 * 7/2001 Matsumoto ............ H04N 19/16
375/240.16
8,401,285 B1 * 3/2013 Rezaee .................... G06T 5/008
382/164

(Continued)

FOREIGN PATENT DOCUMENTS

CN 101366059 A 2/2009
CN 103226575 A 7/2013
(Continued)

OTHER PUBLICATIONS

Zhao, Dayi, DICOM Medical Image Retrieve Based-on Ontology and Similarity Matching, Microcomputer Information, 25(6-3): 306-308, 2009.
(Continued)

*Primary Examiner* — Hadi Akhavannik
(74) *Attorney, Agent, or Firm* — Metis IP LLC

(57) ABSTRACT

A method for generating semantic information may include obtain a scanning image. The scanning image may include a plurality of pixels representing an anatomical structure. The method may also include obtain a trained segmentation model. The method may further include determine a location probability distribution of the anatomical structure in the scanning image based on the trained segmentation model. The method may also include generate a segmentation result related to the anatomical structure based on the location probability distribution. The method may further include save the segmentation result into a tag of a digital imaging and communications in medicine (DICOM) file.

19 Claims, 8 Drawing Sheets

(51) Int. Cl.
  *G06T 7/12* (2017.01)
  *G06T 7/149* (2017.01)
  *G06T 7/70* (2017.01)
  *G16H 30/20* (2018.01)
  *G16H 30/40* (2018.01)
  *G06K 9/62* (2022.01)

(52) U.S. Cl.
  CPC .............. *G06T 7/70* (2017.01); *G16H 30/20* (2018.01); *G16H 30/40* (2018.01); *G06T 2207/10081* (2013.01); *G06T 2207/10104* (2013.01); *G06T 2207/20076* (2013.01); *G06T 2207/20081* (2013.01); *G06T 2207/20084* (2013.01); *G06T 2207/20124* (2013.01); *G06T 2207/30004* (2013.01)

(56) References Cited

U.S. PATENT DOCUMENTS

| | | | |
|---|---|---|---|
| 9,092,691 | B1 | 7/2015 | Beaumont et al. |
| 10,445,462 | B2 * | 10/2019 | Sorenson ................. G06F 40/30 |
| 10,452,813 | B2 * | 10/2019 | Sorenson ................. G16H 15/00 |
| 10,790,056 | B1 * | 9/2020 | Accomazzi .......... G06N 3/0454 |
| 2004/0091153 | A1 * | 5/2004 | Nakano .............. G06K 9/00362 382/228 |
| 2009/0226060 | A1 | 9/2009 | Gering et al. |
| 2010/0111386 | A1 * | 5/2010 | El-Baz ...................... G06T 7/33 382/128 |
| 2010/0157096 | A1 | 6/2010 | Park et al. |
| 2010/0195892 | A1 | 8/2010 | Sato et al. |
| 2013/0035957 | A1 | 2/2013 | Gossler et al. |
| 2015/0131882 | A1 | 5/2015 | Mohr et al. |
| 2015/0261915 | A1 | 9/2015 | Yanagida et al. |
| 2015/0302580 | A1 | 10/2015 | Serlie et al. |
| 2016/0063720 | A1 | 3/2016 | Han et al. |
| 2016/0239956 | A1 * | 8/2016 | Kang ..................... A61B 6/032 |
| 2016/0292876 | A1 | 10/2016 | Zhao |
| 2017/0213339 | A1 * | 7/2017 | Hibbard ................ G06T 7/0012 |
| 2017/0281139 | A1 | 10/2017 | Barbagli et al. |
| 2017/0301081 | A1 | 10/2017 | Yang et al. |
| 2017/0337672 | A1 * | 11/2017 | Zou ........................... G06T 7/35 |
| 2018/0129782 | A1 | 5/2018 | Himsl et al. |
| 2019/0096140 | A1 | 3/2019 | Canfield et al. |

FOREIGN PATENT DOCUMENTS

| | | |
|---|---|---|
| CN | 103340646 A | 10/2013 |
| CN | 104331694 A | 2/2015 |
| CN | 104899926 A | 9/2015 |
| CN | 105389813 A | 3/2016 |
| CN | 106056647 A | 10/2016 |
| CN | 106780520 A | 5/2017 |
| CN | 106821496 A | 6/2017 |
| CN | 107291936 A | 10/2017 |
| CN | 107301645 A | 10/2017 |
| CN | 107833229 A | 3/2018 |
| JP | 2002253539 A | 9/2002 |
| WO | 2016036516 A1 | 3/2016 |
| WO | 2017091833 A1 | 6/2017 |

OTHER PUBLICATIONS

Saif Dawood Salman et al., 3D Brain Segmentation Using Active Contour with Multi Labeling Method, The First National Conference for Engineering Sciences FNCES'12, 2012, 4 pages.
Banerjee Pat et al., A Semi-automated Approach to Improve the Efficiency of Medical Imaging Segmentation for Haptic Rendering, Journal of Digital Imaging, 2017, 9 pages.
The Extended European Search Report in European Application No. 18872844.8 dated Nov. 30, 2020, 8 pages.
Ma, Huibin, Research on Mammary Image Assisted Diagnosis Algorithm Based on Machine Learning, Hunan Normal University Press, 2016, 12 pages.
Chen, Zhaoxue et al., PACS: Medical Image Storage and Communication System, Southeastern University Press, 2016, 18 pages
International Search Report in PCT/CN2018/113618 dated Feb. 3, 2019, 4 pages.
Written Opinion in PCT/CN2018/113618 dated Feb. 3, 2019, 5 pages.
First Office Action in Chinese Application No. 201810988691.9 dated Mar. 3, 2021, 15 pages.
The Second Office Action in Chinese Application No. 201810988691.9 dated Aug. 24, 2021, 26 pages.

* cited by examiner

SYSTEMS AND METHODS FOR GENERATING SEMANTIC INFORMATION FOR SCANNING IMAGE

CROSS-REFERENCE TO RELATED APPLICATIONS

This application is a continuation of International Application No. PCT/CN2018/113618 field on Nov. 2, 2018, which claims priority to Chinese Application No. 201711065915.0, filed on Nov. 2, 2017, and Chinese Application No. 201810988691.9, filed on Aug. 28, 2018, the entire contents of each of which are hereby incorporated by reference.

TECHNICAL FIELD

The present disclosure generally relates to image processing and more specifically relates to systems and methods for generating semantic information for a scanning image.

BACKGROUND

Medical imaging systems (e.g., the computed tomography (CT) system, positron emission tomography (PET) system, magnetic resonance imaging (MRI) system) are often used for medical diagnosis. These medical imaging systems may generate images for the scanning. The images, along with certain information related to the scanning images, may be saved into a digital imaging and communications in medicine (DICOM) file. DICOM is developed to facilitate the communication of images in electronic form and supported by large image management systems called the picture archive and communication systems (PACS).

Semantic information (e.g., a location of an organ, a size of an organ, grey-scale distributions of an organ) of the images may be generated to help a radiologist to diagnose. This process is usually carried by a post-processing workstation to generate the semantic information, which may also require a user's input and be very time-consuming. Therefore, it is desirable to provide an automatic and time-saving method and system for processing scanning images and generate the semantic information of the images.

SUMMARY

In one aspect of the present disclosure, a system is provided. The method may include at least one storage device and at least one processor in communication with the at least one storage device. The at least one storage device may store a set of instructions. When executing the set of instructions, the at least one processor may be configured to cause the system to obtain a scanning image and obtain a trained segmentation model. The scanning image may include a plurality of pixels representing an anatomical structure. The at least one processor may be configured to cause the system to determine a location probability distribution of the anatomical structure in the scanning image based on the trained segmentation model, and generate a segmentation result related to the anatomical structure based on the location probability distribution. The at least one processor may further be configured to cause the system to save segmentation result into a tag of a digital imaging and communications in medicine (DICOM) file.

In some embodiments, the system may include a display. The at least one processor may be further configured to cause the system to generate a marked image based on the segmentation result related to the anatomical structure, and display the marked image to a user by the display.

In some embodiments, the segmentation result may be represented by a contour of the anatomical structure.

In some embodiments, the segmentation result may include at least part of the plurality of pixels representing the anatomical structure. The at least one processor may be further configured to cause the system to extract one or more features related to the anatomical structure based on the segmentation result. The one or more features related to the anatomical structures may include at least one of an average intensity of the at least part of the plurality of pixels representing the anatomical structure; an entropy of the at least part of the plurality of pixels representing the anatomical structure; a homogeneous degree of the at least part of the plurality of pixels representing the anatomical structure; a gray-level co-occurrence matrix of the at least part of the plurality of pixels representing the anatomical structure; a Harr-like feature of the at least part of the plurality of pixels representing the anatomical structure; or a convolution neural network extracted feature of the at least part of the plurality of pixels representing the anatomical structure.

In some embodiments, the trained segmentation model may be generated according to a process for training a segmentation model. The process may include obtaining a preliminary segmentation model; obtaining a plurality of training samples; and training the preliminary segmentation model to obtain the trained segmentation model according to the obtained plurality of training samples.

In some embodiments, the trained segmentation model may be a decision tree model or a neural network model.

In another aspect of the present disclosure, a system is provided. The system may include at least one storage device and at least one processor in communication with the at least one storage device. The at least one storage device may store a set of instructions. When executing the set of instructions, the at least one processor may be configured to cause the system to receive a request for retrieving a target image related to a target anatomical structure from a database containing one or more scanning images; determine a characteristic parameter according to the request; determine a target tag based on the determined characteristic parameter; and retrieve the target image from the database according to the target tag. The one or more scanning images may be processed according to a process for processing an image. The process may include obtaining a scanning image and a trained segmentation model. The scanning image may include a plurality of pixels representing an anatomical structure. The process may also include determining a location probability distribution of the anatomical structure in the scanning image based on the trained segmentation model, and generating a segmentation result related to the anatomical structure based on the location probability distribution. The process may further include saving the segmentation result into a tag of a DICOM file into the database.

In some embodiments, to determine a characteristic parameter according to the request, the at least one processor may be configured to cause the system to determine semantics of the request; and determine the characteristic parameter according to the determined semantics of the request.

In some embodiments, the at least one processor may be further configured to cause the system to retrieve the scanning image, and perform an advanced segmentation on the scanning image based on at least one of Active Shape Model or Optimal Surface Detection.

In another aspect of the present disclosure, a method is provided. The method may be implemented on a computing device having at least one processor and at least one storage device. The method may include obtaining a scanning image, and obtaining a trained segmentation model. The scanning image may include a plurality of pixels representing an anatomical structure. The method may also include determining a location probability distribution of the anatomical structure in the scanning image based on the trained segmentation model, and generating a segmentation result related to the anatomical structure based on the location probability distribution. The method may further include saving the segmentation result into a tag of a DICOM file.

In another aspect of the present disclosure, a method is provided. The method may be implemented on a computing device having at least one processor and at least one storage device. The method may include receiving a request for retrieving a target image related to a target anatomical structure from a database containing one or more scanning images; determining a characteristic parameter according to the request; determining a target tag based on the determined characteristic parameter; and retrieving the target image from the database according to the target tag. The one or more images may be processed according to a process for processing an image. The process may include obtaining a scanning image, the scanning image including a plurality of pixels representing an anatomical structure; obtaining a trained segmentation model; determining a location probability distribution of the anatomical structure in the scanning image based on the trained segmentation model; generating a segmentation result related to the anatomical structure based on the location probability distribution; and saving the segmentation result into a tag of a DICOM file into the database.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "unit," "module," and/or "block" used herein are one method to distinguish different components, elements, parts, section or assembly of different level in ascending order. However, the terms may be displaced by another expression if they achieve the same purpose.

Figure 2:
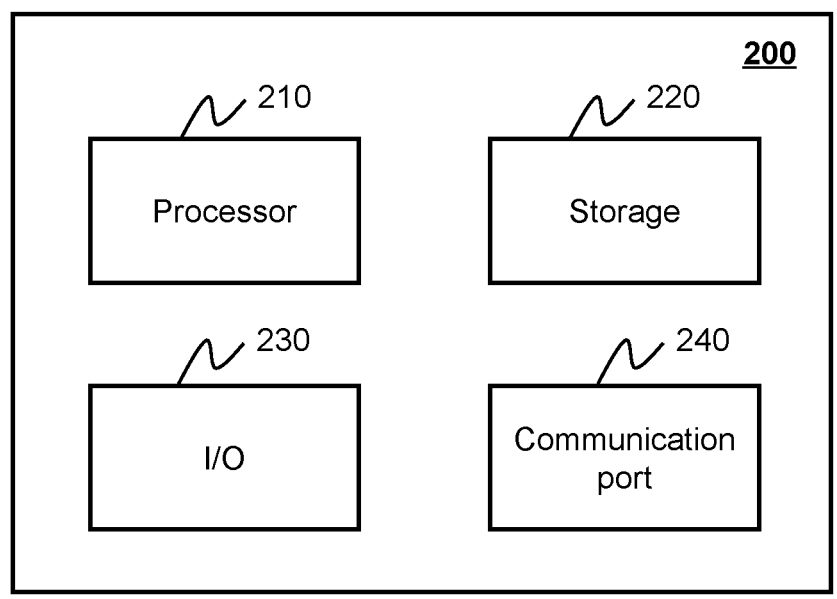
FIG. 2 is a schematic diagram illustrating exemplary hardware and/or software components of a computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included of connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

An aspect of the present disclosure relates to systems and methods for generating semantic information for a scanning image. The systems and methods may obtain a scanning image and a trained segmentation model. The scanning image may be generated by a computed tomography (CT) system. The trained segmentation model may be generated by training a preliminary segmentation model using a plurality of training samples (e.g., a plurality of sample images). The systems and methods may determine a location probability distribution of the anatomical structure in the scanning image based on the trained segmentation model, and further generate a segmentation result related to the anatomical structure based on the location probability distribution. The systems and methods may extract one or more features related to the anatomical structure based on the segmentation result. The systems and methods may generate a tag for the scanning image based on the segmentation result and the one or more features. In some embodiments, the scanning image and the corresponding tag may be saved into a DICOM file and/or stored in PACS or a local folder for retrieval (e.g., semantic retrieval) or advanced post-processing (e.g., accelerated post-processing).

The following description is provided to help better understanding the generation of a tag for a scanning image. This is not intended to limit the scope the present disclosure. For persons having ordinary skills in the art, a certain amount of variations, changes, and/or modifications may be deducted under the guidance of the present disclosure. Those variations, changes, and/or modifications do not depart from the scope of the present disclosure.

Figure 1:
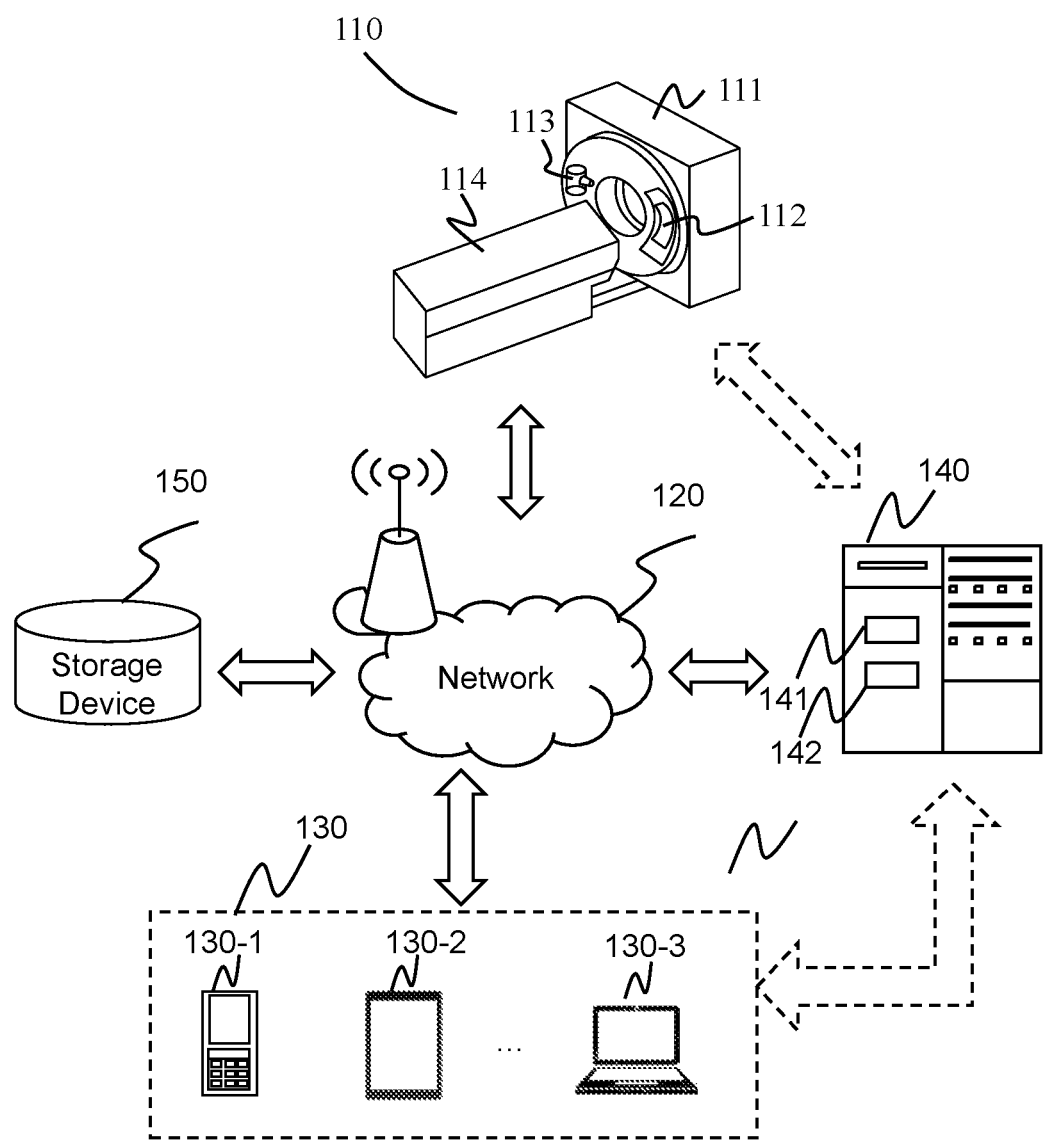
FIG. 1 is a schematic diagram illustrating an exemplary medical imaging system according to some embodiments of the present disclosure.

FIG. 1 is schematic diagrams illustrating an exemplary medical imaging system 100 according to some embodiments of the present disclosure. The medical imaging system 100 may include but is not limited to a computed tomography (CT) system, a computed tomography angiography (CTA) system, a positron emission tomography (PET) system, a single photon emission computed tomography (SPECT) system, a magnetic resonance imaging (MRI) system, a digital subtraction angiography (DSA) system, an ultrasonic scanning (US) system, a thermal texture map (TTM) system, etc. In some embodiments, the medical imaging system may be solely used. In some embodiments, the medical imaging system may be used with a combination (e.g., a PET-CT system).

As illustrated in FIG. 1, the medical imaging system 100 may include a scanner 110, a network 120, a terminal 130, a processing device 140, and a storage device 150. The components in the medical imaging system 100 may be connected in various ways. Merely by way of example, the scanner 110 may be connected to the processing device 140 through the network 120. As another example, the scanner 110 may be connected to the processing device 140 directly as indicated by the bi-directional arrow in dotted lines linking the scanner 110 and the processing device 140. As a further example, the storage device 150 may be connected to the processing device 140 directly or through the network 120. As still a further example, the terminal 130 may be connected to the processing device 140 directly (as indicated by the bi-directional arrow in dotted lines linking the terminal 130 and the processing device 140) or through the network 120.

Taking a CT system as an example, as illustrated in FIG. 1, the scanner 110 may include a gantry 111, a detector 112, a radiation source 113, and a scanning table 114. The detector 112 and the radiation source 113 may be oppositely mounted to the gantry 111. The radiation source 113 may emit radiation rays to scan an object that is placed on the scanning table 114. The radiation rays may include X-rays, y-rays, a-rays, ultraviolet, laser, neutron, proton, or the like, or any combination thereof. The object may be a biological object (e.g., a patient, an animal) or a non-biological object (e.g., a phantom). In the present disclosure, "object" and "subject" are used interchangeably. The detector 112 may detect radiations (e.g., X-rays) passed through the object. In some embodiments, the detector 112 may include a plurality of detector units. The detector units may include a scintillation detector (e.g., a cesium iodide detector) or a gas detector. The detector units may be arranged in a single row or multiple rows. In some embodiments, the radiation source 113 may be omitted in some medical imaging systems, for example, in a PET system. In the PET system, the object may be injected with a radioactive substance (e.g., radiopharmaceutical). The detector 112 may detect radiation (e.g., gamma photons) emitted from the radioactive substance.

The network 120 may facilitate exchange of information and/or data. In some embodiments, one or more components in the medical imaging system 100 (e.g., the scanner 110, the terminal 130, the processing device 140, or the storage device 150) may send information and/or data to another component(s) in the medical imaging system 100 via the network 120. For example, the processing device 140 may obtain scanning data from the scanner 110 via the network 120. As another example, the processing device 140 may obtain user instructions from the terminal 130 via the network 120. In some embodiments, the network 120 may be any type of wired or wireless network, or combination thereof. The network 120 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 120 may include a cable network, a wireline network, an optical fiber network, a tele communications network, an intranet, an Internet, a local area network (LAN), a wide area network (WAN), a wireless local area network (WLAN), a metropolitan area network (MAN), a wide area network (WAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired or wireless network access points such as base stations and/or internet exchange points through which one or more components of the medical imaging system 100 may be connected to the network 120 to exchange data and/or information.

The terminal 130 include a mobile device 130-1, a tablet computer 130-2, a laptop computer 130-3, or the like, or any combination thereof. In some embodiments, the mobile device 130-1 may include a smart home device, a wearable device, a smart mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a smart bracelet, smart footgear, a pair of smart glasses, a smart helmet, a smartwatch, smart clothing, a smart backpack, a smart accessory, or the like, or any combination thereof. In some embodiments, the smart mobile device may include a smartphone, a personal digital assistant (PDA), a gaming device, a navigation device, a point of sale (POS) device, or the like, or any combination thereof. In some embodiments, the virtual reality device and/or the augmented reality device may include a virtual reality helmet, a virtual reality glass, a virtual reality patch, an augmented reality helmet, an augmented reality glass, an augmented reality patch, or the like, or any combination thereof. For example, the virtual reality device and/or the augmented reality device may include a Google Glass, an Oculus Rift, a Hololens, a Gear VR, etc. In some embodiments, the terminal 130 may remotely operate the scanner 110. In some embodiments, the terminal 130 may operate the scanner 110 via a wireless connection. In some embodiments, the terminal 130 may receive information and/or instructions inputted by a user, and send the received information and/or instructions to the scanner 110 or the processing device 140 via the network 120. In some embodiments, the terminal 130 may receive data and/or information from the processing device 140. In some embodiments, the terminal 130 may be part of the processing device 140. In some embodiments, the terminal 130 may be omitted.

In some embodiments, the processing device 140 may include a processing engine 141 and/or a processing engine 142. The processing device 140 (e.g., the processing engine 141 and/or the processing engine 142) may process data obtained from the scanner 110, the terminal 130, or the storage device 150. For example, the processing engine 141 may obtain a scanning image and a trained segmentation model. Then the processing engine 141 may generate a tag for the scanning image based on the trained segmentation model. The processing engine 142 may be configured to generate a trained segmentation model (e.g., the trained segmentation model described above) by training a preliminary segmentation model using a plurality of training samples.

The processing device 140 may be a central processing unit (CPU), a digital signal processor (DSP), a system on a chip (SoC), a microcontroller unit (MCU), or the like, or any combination thereof. In some embodiments, the processing device 140 may be a single server or a server group. The server group may be centralized or distributed. In some embodiments, the processing device 140 may be local or remote. For example, the processing device 140 may access information and/or data stored in the scanner 110, the terminal 130, and/or the storage device 150 via the network 120. As another example, the processing device 140 may be directly connected to the scanner 110, the terminal 130, and/or the storage device 150, to access stored information and/or data. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented on a computing device 200 having one or more components illustrated in FIG. 2 in the present disclosure.

The storage device 150 may store data and/or instructions. In some embodiments, the storage device 150 may store data obtained from the terminal 130 and/or the processing device 140. In some embodiments, the storage device 150 may store data and/or instructions that the processing device 140 may execute or use to perform exemplary methods described in the present disclosure. In some embodiments, the storage device 150 may include a mass storage, removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more components in the medical imaging system 100 (e.g., the terminal 130, the processing device 140). One or more components in the medical imaging system 100 may access the data or instructions stored in the storage device 150 via the network 120. In some embodiments, the storage device 150 may be directly connected to or communicate with one or more components in the medical imaging system 100 (e.g., the terminal 130, the processing device 140). In some embodiments, the storage device 150 may be part of the processing device 140.

FIG. 2 is a schematic diagram illustrating exemplary hardware and/or software components of a computing device 200 on which the processing device 140 (e.g., the processing engine 141, the processing engine 142) may be implemented according to some embodiments of the present disclosure. As illustrated in FIG. 2, the computing device 200 may include a processor 210, a storage 220, an input/output (I/O) 230, and a communication port 240.

The processor 210 may execute computer instructions (program code) and perform functions of the processing device 140 in accordance with techniques described herein. The computer instructions may include, for example, routines, programs, objects, components, signals, data structures, procedures, modules, and functions, which perform particular functions described herein. For example, the processor 210 may process data obtained from the scanner 110, the terminal 130, the storage device 150, and/or any other component of the medical imaging system 100. In some embodiments, the processor 210 may generate a tag for a scanning image that obtained from the scanner 110. In some embodiments, the scanning image and the corresponding tag may be saved into a digital imaging and communications in medicine (DICOM) file, and further stored on a picture archiving and communication system (PACS) or a local folder for retrieval (e.g., semantic retrieval) or advanced post-processing (e.g., accelerated post-processing). In some embodiments, the scanning image and the corresponding tag may be displayed on a display device by the I/O 230. In some embodiments, the processor 210 may perform instructions obtained from the terminal 130. For example, the processor 210 may retrieve a target image based on a request received from the terminal 130. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors; thus operations and/or method steps that are performed by one processor as described in the present disclosure may also be jointly or separately performed by the multiple processors. For example, if in the present disclosure the processor of the computing device 200 executes both process A and process B, it should be understood that process A and process B may also be performed by two or more different processors jointly or separately in the computing device 200 (e.g., a first processor executes process A and a second processor executes process B, or the first and second processors jointly execute processes A and B).

The storage 220 may store data/information obtained from the scanner 110, the terminal 130, the storage device 150, or any other component of the medical imaging system 100. In some embodiments, the storage 220 may include a mass storage device, a removable storage device, a volatile read-and-write memory, a read-only memory (ROM), or the like, or any combination thereof. For example, the mass storage may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure. For example, the storage 220 may store a program for the processing engine 141 for generating a tag for a scanning image. As another example, the storage 220 may store a program for the processing engine 142 for generating a trained segmentation model.

The I/O 230 may input or output signals, data, and/or information. In some embodiments, the I/O 230 may enable user interaction with the processing device 140. In some embodiments, the I/O 230 may include an input device and an output device. Exemplary input devices may include a keyboard, a mouse, a touch screen, a microphone, or the like, or a combination thereof. Exemplary output devices may include a display device, a loudspeaker, a printer, a projector, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

The communication port 240 may be connected to a network (e.g., the network 120) to facilitate data communications. The communication port 240 may establish connections between the processing device 140 and the scanner 110, the terminal 130, or the storage device 150. The connection may be a wired connection, a wireless connection, or combination of both that enables data transmission and reception. The wired connection may include an electrical cable, an optical cable, a telephone wire, or the like, or any combination thereof. The wireless connection may include Bluetooth, Wi-Fi, WiMax, WLAN, ZigBee, mobile network (e.g., 3G, 4G, 5G, etc.), or the like, or a combination thereof. In some embodiments, the communication port 240 may be a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
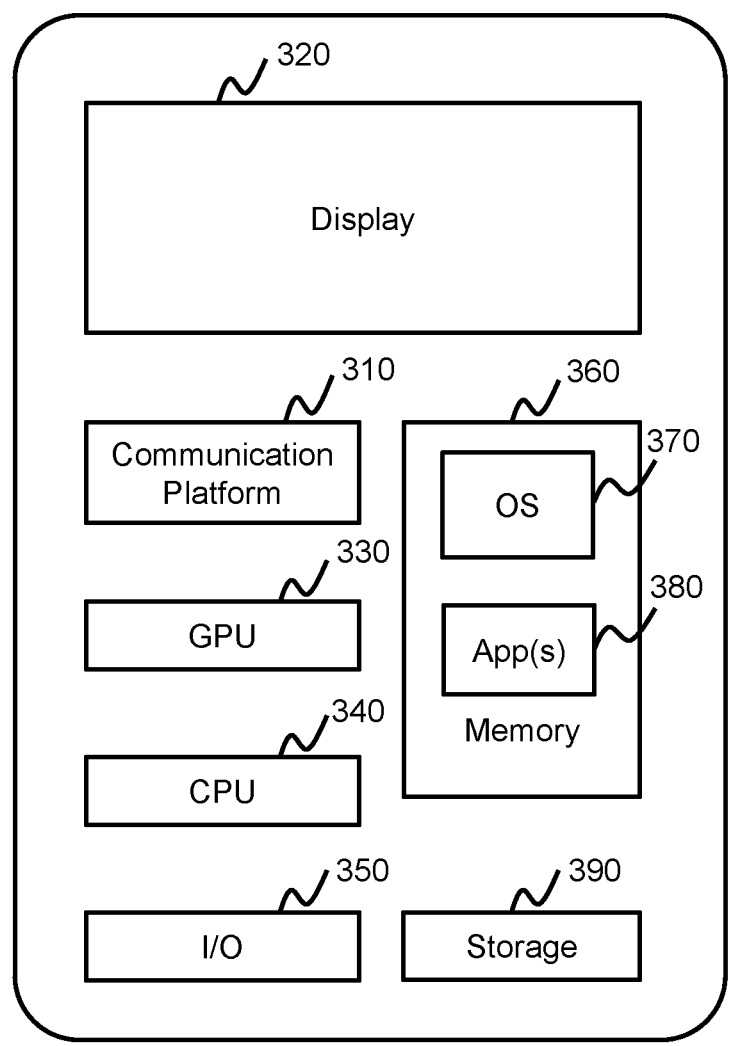
FIG. 3 is a schematic diagram illustrating exemplary hardware and/or software components of a mobile device according to some embodiments of the present disclosure.

FIG. 3 is a schematic diagram illustrating exemplary hardware and/or software components of a mobile device 300 according to some embodiments of the present disclosure. As illustrated in FIG. 3, the mobile device 300 may include a communication platform 310, a display 320, a graphics processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS, Android, Windows Phone, etc.) and one or more applications 380 may be loaded into the memory 360 from the storage 390 in order to be executed by the CPU 340. The applications 380 may include a browser or any other suitable mobile apps for receiving and rendering information relating to image processing or other information from the processing device 140 (e.g., the processing engine 141, the processing engine 142). User interactions with the information stream may be achieved via the I/O 350 and provided to the processing device 140 and/or other components of the medical imaging system 100 via the network 120.

To implement various modules, units, and their functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar therewith to adapt those technologies to generate a tag for a scanning image as described herein. A computer with user interface elements may be used to implement a personal computer (PC) or another type of work station or terminal device, although a computer may also act as a server if appropriately programmed. Those skilled in the art are familiar with the structure, programming and general operation of such computer equipment and as a result, the drawings should be self-explanatory.

Figure 4:
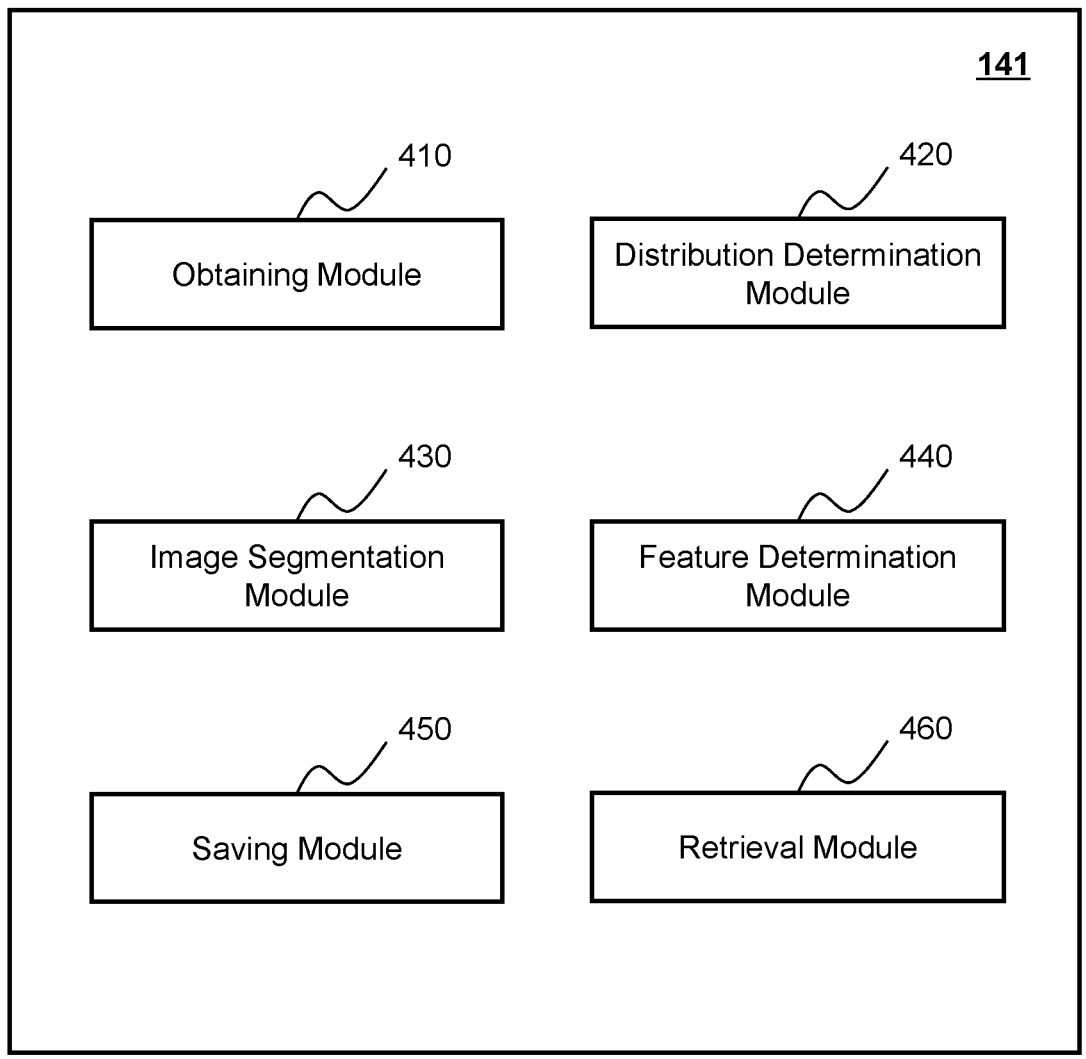
FIG. 4 is a block diagram illustrating an exemplary processing device according to some embodiments of the present disclosure.

FIG. 4 is a block diagram illustrating an exemplary processing device (e.g., the processing engine 141) according to some embodiments of the present disclosure. The processing engine 141 may be implemented on the computing device 200 (e.g., the processor 210) as illustrated in FIG. 2. The processing engine 141 may include an acquisition module 410, a distribution determination module 420, an image segmentation module 430, a feature determination module 440, a saving module 450, and a retrieval module 460.

The acquisition module 410 may be configured to obtain information related to the scanner 110. The information related to the scanner 110 may include scan data, image data, or the like. For example, the acquisition module 410 may obtain a scanning image. The scanning image may include a plurality of pixels representing an anatomical structure. In some embodiments, the scanning image may be a two-dimensional (2D) image, a three-dimensional (3D) image, or the like. In some embodiments, the anatomical structure may include gas in the patient (e.g., air), liquid in the patient (e.g., water), solid in the patient (e.g., a stone or a calculus), cell(s) of a patient, tissue(s) of the patient, one or more organs of the patient, or the like, or any combination thereof, which displayed in the scanning image, or really existing in or on the patient's body. Each of the plurality of pixels may have a pixel value referring to the value of a property of a pixel. In some embodiments, the acquisition module 410 may directly obtain the scanning image via the scanner 110, or via a storage device (e.g., the storage device 150).

The acquisition module 410 may also be configured to obtain a model (e.g., a trained segmentation model). The trained segmentation model may relate to an anatomical structure of interest (ASI) represented by a plurality of pixels in a plurality of sample images. For example, a plurality of sample images containing the ASI may be designated as training samples used to generate the trained segmentation model. The ASI may include one or more particular organs of the anatomical structure, for example, a heart, a stomach. The trained segmentation model may be used to determine a probability of a pixel that belongs to the ASI. In some embodiments, the trained segmentation model may be generated by the processing engine 142 (e.g., by one or more modules of the processing engine 142). In some embodiments, the acquisition module 410 may obtain a plurality of trained segmentation models. Each trained segmentation model may be related to an ASI containing one or more organs. The trained segmentation models may include one or more same or different organs. In some embodiments, one trained segmentation model may only include a part of the anatomical structure in the scanning image, and the trained segmentation model may be used to determine probabilities of pixels in the part of the scanning image. Other trained segmentation model(s) may include other part(s) of the anatomical structure in the scanning image, and the trained segmentation model(s) may be used to determine probabilities of pixels in the other part(s) of the scanning image.

The distribution determination module 420 may be configured to determine a location probability distribution of the anatomical structure in the scanning image based on the trained segmentation model. In some embodiments, the scanning image may be inputted into the trained segmentation model that related to an ASI containing one or more organs. The distribution determination module 420 may determine probabilities of the plurality of pixels in the scanning image that belong to the ASI (e.g., the one or more organs) according to the trained segmentation model. The probabilities of pixels may be values between 0 and 100%. Merely by way of example, the distribution determination module 420 may compare the pixel value of a pixel in the scanning image with the pixel values of pixels related to the ASI according to the trained segmentation model. According to a result of the comparison, the distribution determination module 420 may determine a probability of the pixel belonging to the ASI based on the trained segmentation model, and the probability of the pixel may be a value between 0 and 100%.

In some embodiments, the distribution determination module 420 may only determine multiple probabilities of pixels in a part of the scanning image based on one trained segmentation model, and the distribution determination module 420 may determine multiple probabilities of pixels in other part(s) of the scanning image based on other trained segmentation model(s). In some embodiments, each pixel in the scanning image may be given a probability between 0 and 100%. The probabilities of the pixels that totally belong to an organ of the ASI may be designated as 100%, and the probabilities of the pixels that do not belong to any organ of the ASI may be designated as 0. The distribution determination module 420 may determine the location probability distribution of the anatomical structure in the scanning image based on the plurality of probabilities of the pixels.

The image segmentation module 430 may be configured to generate a segmentation result related to the anatomical structure based on the location probability distribution. The location probability distribution may include a plurality of probabilities of the pixels. The image segmentation module 430 may generate a segmentation result based on the plurality of probabilities of the pixels. For example, if the probability of a pixel belonging to an organ (e.g., a heart) is 100%, the image segmentation module 430 may label the pixel with the name of the organ (e.g., "heart"). As another example, if the probability of a pixel belonging to the first organ (e.g., a liver) is 80% and the probability of the pixel belonging to the second organ (e.g., a stomach) is 20%, the image segmentation module 430 may label the pixel with the name of the first organ (e.g., "liver"). As a further example, if the probability of a pixel belonging to an ASI containing one or more organs is 0, the image segmentation module 430 may not label the pixel. Thus, a subset of the pixels in the scanning image may be labeled with the name of one of the organs, and the rest of the pixels in the scanning image may not be labeled. In some embodiments, the image segmentation module 430 may designate the pixels labeled with the name of an organ as the organ. The image segmentation module 430 may determine one or more organs based on the labeled pixels. The image segmentation module 430 may determine a segmentation result based on the one or more organs. The segmentation result may include information related to one or more organs. In some embodiments, the segmentation result may be represented by a mask, a contour, or a mesh.

The feature determination module 440 may be configured to extract one or more features related to the anatomical structure based on the segmentation result. In some embodiments, the segmentation result may include the information related to one or more organs. For each organ, the feature determination module 440 may determine one or more features related to the organ. In some embodiments, the segmentation result may include at least part of the plurality of pixels that represent the anatomical structure. The one or more features related to the anatomical structure may include the average intensity of the at least part of the plurality of pixels representing the anatomical structure, the entropy of the at least part of the plurality of pixels representing the anatomical structure, the homogeneous degree of the at least part of the plurality of pixels representing the anatomical structure, the gray-level co-occurrence matrix of the at least part of the plurality of pixels representing the anatomical structure, a textural feature of the at least part of the plurality of pixels representing the anatomical structure, a Gabor filter-based textural feature of the at least part of the plurality of pixels representing the anatomical structure, a Harr-like feature of the at least part of the plurality of pixels representing the anatomical structure, a convolution neural network extracted feature of the at least part of the plurality of pixels representing the anatomical structure, or the like, or any combination thereof. In some embodiments, the gray-level co-occurrence matrix may be represented by energy related to an image, entropy related to the image, moments related to the image, correlation quantity related to the image. The Tamura textural feature may be represented by the coarseness of an image, contrast of the image, directionality of the image, line likeness of the image, regularity of the image, roughness of the image.

In some embodiments, the feature information may be used to determine pathological information related to one or more organs (e.g., nodule, tumor, stone). Alternatively or additionally, the feature information may be used to determine density information related to tissues (e.g., the density of fat, the density of air, the density of water). In some embodiments, the feature information may be used to determine specific parts of the one or more organs (e.g., the top of the liver, the bottom of the liver).

The saving module 450 may be configured to save the segmentation result and/or the one or more features into a tag of a digital imaging and communications in medicine (DICOM) file. The tag may correspond to the scanning image. The tag may include the names of the one or more organs, the locations of the one or more organs, the sizes of the one or more organs, the shapes of the one or more organs, the features of the one or more organs, information related to pixels that belong to the one or more organs, or the like, or any combination thereof. In some embodiments, if the scanning image is a 2D image, the tag may include layer information. If the scanning image is a 3D image, the tag may include layer information, volume data information. The saving module 450 may receive the segmentation result generated by the image segmentation module 430, and save the segmentation result into a tag of a DICOM file. In some embodiments, the saving module 450 may further store the DICOM file on a picture archiving and communication system (PACS) or a local folder for retrieval (e.g., semantic retrieval) or advanced post-processing (e.g., accelerated post-processing).

The retrieval module 460 may be configured to retrieve a target image. The retrieval module 460 may first receive a request for retrieving a target image, for example, from a user (e.g., a doctor) via a user interface (e.g., the I/O 230). The request may relate to retrieving the target image containing a target anatomical structure from one or more scanning images. The target anatomical structure may include one or more target organs. Each of the one or more scanning images may include a tag, including the names of an ASI (e.g., one or more organs), the locations of the ASI (e.g., the one or more organs), the sizes of the ASI (e.g., the one or more organs), the shapes of the ASI (e.g., the one or more organs), the features of the ASI (e.g., the one or more organs), information related to pixels representing the ASI (e.g., the one or more organs), etc. In some embodiments, the tag may include layer information, volume data information, or the like.

The retrieval module 460 may determine a characteristic parameter according to the request. The retrieval module 460 may determine the semantics of the request, and determine the characteristic parameter according to the determined semantics of the request. The characteristic parameter may relate to a characteristic of the target anatomical structure. In some embodiments, the characteristic parameter may be determined based on clinical empirical values, or may be default settings of semantics, or may be adjusted by a user (e.g., a doctor). The retrieval module 460 may also determine a target tag based on the determined characteristic parameter. In some embodiments, the target tag may include the name of the target anatomical structure, the location of the target anatomical structure, the size of the target anatomical structure, the shape of the target anatomical structure, the features of the target anatomical structure, information related to pixels representing the target anatomical structure, etc. For example, for the request with the semantics of "splenomegaly," the target tag may include the name of the target anatomical structure "spleen," information related to the size of the target anatomical structure (e.g., the size larger than a first threshold). As another example, for the request with the semantics of "fatty liver," the target tag may include the name of the target anatomical structure "liver," information related to a gray average of the pixels representing the liver (e.g., the gray average of the pixels less than a second threshold).

The retrieval module 460 may retrieve the target image according to the target tag. In some embodiments, the retrieval module 460 may retrieve the target image by traversing the one or more scanning images according to the target tag. For example, for the request with the semantics of "splenomegaly," the retrieval module 460 may select images that contain spleen with a size larger than the first threshold from the one or more scanning images as the target image. As another example, for the request with the semantics of "fatty liver," the retrieval module 460 may select images that contain liver with an average intensity of pixels less than the second threshold from the one or more scanning images as the target image.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. Two or more of the modules may be combined as a single module. For example, the distribution determination module 420 may be integrated into the image segmentation module 430 as a single module that may determine a location probability distribution of anatomical structure and generate a segmentation result related to the anatomical structure. An individual module may be divided into two or more units. For example, the acquisition module 410 may be divided into a first unit and a second unit. The first unit may be configured to obtain the scanning image, and the second unit may be configured to obtain the trained segmentation module. In some embodiments, the processing engine 141 may further include one or more other modules. For example, the processing engine 141 may further include a storage module (not shown in FIG. 4). The storage module may be configured to store data generated during any process performed by any component of in the processing engine 141. As another example, each of components of the processing engine 141 may include a storage apparatus. Additionally or alternatively, the components of the processing engine 141 may share a storage apparatus.

Figure 5:
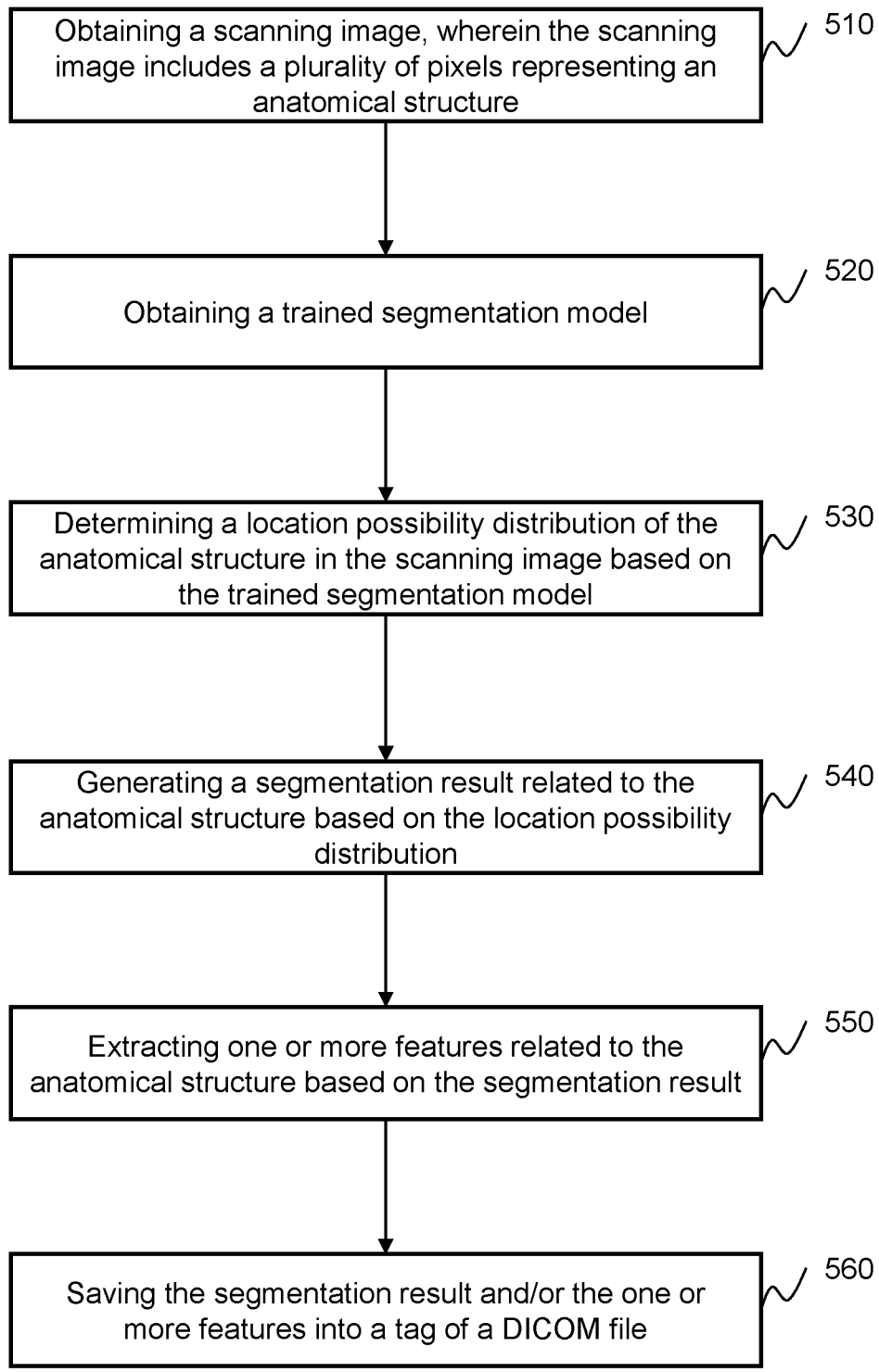
FIG. 5 is a flowchart illustrating an exemplary process for saving a segmentation result of a scanning image according to some embodiments of the present disclosure.

FIG. 5 is a flowchart illustrating an exemplary process for saving a segmentation result of a scanning image according to some embodiments of the present disclosure. The process 500 may be implemented in the medical imaging system 100 illustrated in FIG. 1. For example, the process 500 may be stored in the storage device 150 and/or the storage 220 in the form of instructions (e.g., an application), and invoked and/or executed by the processing device 140 (e.g., the processor 210 illustrated in FIG. 2, or one or more modules in the processing engine 141 illustrated in FIG. 4). The operations of the illustrated process presented below are intended to be illustrative. In some embodiments, the process 500 may be accomplished with one or more additional operations not described, and/or without one or more of the operations discussed. Additionally, the order in which the operations of the process 500 as illustrated in FIG. 5 and described below is not intended to be limiting.

In 510, the acquisition module 410 may obtain a scanning image. The scanning image may include a plurality of pixels representing an anatomical structure. In some embodiments, the scanning image may be a two-dimensional (2D) image, a three-dimensional (3D) image, or the like. In some embodiments, the anatomical structure may include gas in the patient (e.g., air), liquid in the patient (e.g., water), solid in the patient (e.g., a stone or a calculus), cells of a patient, tissue of the patient, one or more organs of the patient, or the like, or any combination thereof, which displayed in the scanning image, or really existing in or on the patient's body. Each of the plurality of pixels may have a pixel value referring to the value of a property of a pixel. For instance, a pixel value may refer to the luminance value of the pixel, the grey-scale value of the pixel, the color or RGB value of the pixel, the saturation value of the pixel, or the like, or a combination thereof. In some embodiments, the acquisition module 410 may directly obtain the scanning image from the scanner 110. Alternatively, the acquisition module 410 may obtain the scanning image from a storage device (e.g., the storage device 150).

In 520, the acquisition module 410 may obtain a trained segmentation model. The trained segmentation model may relate to an anatomical structure of interest (ASI) represented by a plurality of pixels in a plurality of sample images. In some embodiments, the plurality of sample images containing the ASI may be designated as training samples used to generate the trained segmentation model. The ASI may include a particular organ of the anatomical structure. For example, the ASI may be a heart. Alternatively, the ASI may include more than one particular organ of the anatomical structure. For example, the ASI may include a heart, a stomach, etc. The trained segmentation model may be used to determine a probability of a pixel that belongs to the ASI. Specifically, the trained segmentation model may be used to determine a probability of a pixel that belongs to one or more organs (e.g., a heart, a stomach). In some embodiments, the trained segmentation model may be generated by the processing engine 142 (e.g., by one or more modules of the processing engine 142). The trained segmentation model may be determined according to an exemplary process 700 illustrated in FIG. 7.

In some embodiments, exemplary trained segmentation models may include a Ranking Support Vector Machine (SVM) model, a decision tree model (e.g., a Gradient Boosting Decision Tree (GBDT) model), a LambdaMART model, an adaptive boosting model, a hidden Markov model, a Hopfield network model, a self-organizing map (SOM), a learning vector quantization (LVQ), a convolutional neural network model (e.g., a multi-scale convolutional neural network model, a super-resolution convolutional neural network model, a denoising convolutional neural network model), a perceptron neural network model, a deep trust network model, a stack self-coding network model, a recurrent neural network model (e.g., a long short term memory (LSTM) neural network model, a hierarchical recurrent neural network model, a bi-direction recurrent neural network model, a second-order recurrent neural network model, a fully recurrent network model, an echo state network model, a multiple timescales recurrent neural network (MTRNN) model), or the like, or any combination thereof.

In some embodiments, the acquisition module 410 may obtain a plurality of trained segmentation models. Each trained segmentation model may be related to an ASI containing one or more organs. The trained segmentation models may include one or more same or different organs. For example, a first trained segmentation model may include a heart, and a second trained segmentation model may include a stomach. As another example, the first trained segmentation model may include a heart and a stomach, and the second trained segmentation model may include a stomach and a liver. In some embodiments, one trained segmentation model may only include a part of the anatomical structure in the scanning image, and the trained segmentation model may be used to determine probabilities of pixels in the part of the scanning image. Other trained segmentation model(s) may include other part(s) of the anatomical structure in the scanning image, and the trained segmentation model(s) may be used to determine probabilities of pixels in the other part(s) of the scanning image.

In 530, the distribution determination module 420 may determine a location probability distribution of the anatomical structure in the scanning image based on the trained segmentation model. In some embodiments, the scanning image may be inputted into the trained segmentation model that related to an ASI containing one or more organs. The distribution determination module 420 may determine probabilities of the plurality of pixels in the scanning image that belong to the ASI (e.g., the one or more organs) according to the trained segmentation model. The probabilities of pixels may be values between 0 and 100%. Merely by way of example, the distribution determination module 420 may compare the pixel value of a pixel in the scanning image with the pixel values of pixels related to an ASI according to the trained segmentation model. According to a result of the comparison, the distribution determination module 420 may determine a probability of the pixel being belonging to the ASI based on the trained segmentation model, and the probability of the pixel may be a value between 0 and 100%. The pixel values of pixels in different organs may be different, but the pixel values of pixels in an organ may be substantially the same. Thus, in the trained segmentation model, an average pixel value of pixels of an organ may be used to represent the organ. The ASI may include one or more organs, and one or more average pixel values of pixels related to the ASI (or the one or more organs) may be determined in the trained segmentation model. Merely by way of example, the distribution determination module 420 may determine whether the pixel value of the pixel in the scanning image is the same or substantially the same as the average pixel values of pixels related to the ASI (or the one or more organs) according to the trained segmentation model. In response to the determination that the pixel value of the pixel in the scanning image is the same as or substantially the same as an average pixel value of the pixels related to an organ of the ASI, the distribution determination module 420 may determine the probability of the pixel belonging to the organ may be 100%. In response to the determination that the pixel value of the pixel in the scanning image is different from the average pixel values of the pixels related to the ASI (or the one or more organs), the distribution determination module 420 may determine the probability of the pixel belonging to the AIS (or any organ) may be a value between 0 and 100%. Merely by way of example, the distribution determination module 420 may determine one or more differences between the pixel value of the pixel in the scanning image and the average pixel values of pixels related to one or more organs. The distribution determination module 420 may determine whether the one or more differences are less than a threshold. The threshold may be a default value determined by the scanner 110 or adjusted by a user (e.g., a doctor). In response to the determination that the one or more differences are greater than the threshold, the distribution determination module 420 may determine the probability of the pixel belonging to the ASI may be 0. In response to the determination that one difference is less than the threshold, the distribution determination module 420 may determine the probability of the pixel belonging to an organ corresponding to the difference may be 100%. In response to the determination that at least two differences are less than the threshold, the distribution determination module 420 may determine the probabilities of the pixel belonging to at least two organs corresponding to the at least two differences may be a value larger than 0 and less than 100%. For example, the probability of the pixel belonging to the first organ may be 80%, and the probability of the pixel belonging to the second organ may be 20%. It should be noted that the descriptions of the probability of the pixel above are merely examples and are not intended to limit the scope of the present disclosure.

In some embodiments, the distribution determination module 420 may determine multiple probabilities of pixels in a part of the scanning image based on one trained segmentation model, and the distribution determination module 420 may determine multiple probabilities of pixels in other part(s) of the scanning image based on other trained segmentation model(s). For example, if a first trained segmentation model is related to a first organ (e.g., a heart), the distribution determination module 420 may determine multiple probabilities of pixels near the first organ (e.g., the heart) in the scanning image according to the first trained segmentation model. Similarly, if a second trained segmentation model is related to a second organ (e.g., a stomach), the distribution determination module 420 may determine multiple probabilities of pixels near the second organ (e.g., the stomach) in the scanning image according to the second trained segmentation model. Finally, each pixel in the scanning image may be given a probability between 0 and 100%. In particular, the probabilities of the pixels being belonging to an organ may be designated as 100%, and the probabilities of the pixels that do not belong to any organ of the ASI may be designated as 0. The distribution determination module 420 may determine the location probability distribution of the anatomical structure in the scanning image based on the plurality of probabilities of the pixels. In some embodiments, the distribution determination module 420 may determine the location probability distribution in the form of tables, graphs, charts, or a combination thereof.

In 540, the image segmentation module 430 may generate a segmentation result related to the anatomical structure based on the location probability distribution. The location probability distribution may include a plurality of probabilities of the pixels. The image segmentation module 430 may generate a segmentation result based on the plurality of probabilities of the pixels. For example, if the probability of a pixel belonging to an organ (e.g., a heart) is 100%, the image segmentation module 430 may label the pixel with the name of the organ (e.g., "heart"), and in general, the pixel may be located in an internal part of the organ. As another example, if the probability of a pixel belonging to the first organ (e.g., a liver) is 80% and the probability of the pixel belonging to the second organ (e.g., a stomach) is 20%, the image segmentation module 430 may label the pixel with the name of the first organ (e.g., "liver"), and in general, the pixel may be located at a boundary position of the two organs. As a further example, if the probability of a pixel belonging to an ASI is 0, the image segmentation module 430 may not label the pixel. Thus, a subset of the pixels in the scanning image may be labeled with the name of one of the organs, and the rest of the pixels in the scanning image may not be labeled. In some embodiments, the image segmentation module 430 may designate the pixels labeled with the name of an organ as the organ. The image segmentation module 430 may determine one or more organs based on the labeled pixels. The image segmentation module 430 may also determine a segmentation result based on the one or more organs. The segmentation result may be represented by a mask or a contour. In some embodiments, if the segmentation result is displayed in the form of a mask, for each of the organs, the pixels belonging to an organ may be marked with the name of that organ. In some embodiments, if the segmentation result is represented by a contour, for each of the organs, the pixels representing a contour of an organ may be marked with name of that organ (e.g., a contour of a heart may be marked by "heart"). Alternatively, the segmentation result may be represented as a mesh that corresponds to a computer model for computational fluid dynamics (CFD) and finite element analysis (FEA). For example, for an organ (e.g., a heart), the pixels that belong to the organ may be divided into meshes by performing a meshing algorithm, such as a triangle meshing. The segmentation result may include the meshes corresponding to one or more organs.

In some embodiments, a marked image may be generated based on the segmentation result related to the anatomical structure. Mere by way of example, if the segmentation result is represented by one or more contours corresponding to one or more organs, the marked image may include the one or more contours and one or more corresponding names of organs. In some embodiments, the marked image may be displayed to a user (e.g., a doctor) for further analysis or process.

In 550, the feature determination module 440 may extract one or more features related to the anatomical structure based on the segmentation result. In some embodiments, the segmentation result may include the information related to one or more organs. For each organ, the feature determination module 440 may determine one or more features related to the organ. In some embodiments, the segmentation result may include at least part of the plurality of pixels that represent the anatomical structure. The one or more features related to the anatomical structure may include the average intensity of the at least part of the plurality of pixels representing the anatomical structure, the entropy of the at least part of the plurality of pixels representing the anatomical structure, the homogeneous degree of the at least part of the plurality of pixels representing the anatomical structure, the gray-level co-occurrence matrix of the at least part of the plurality of pixels representing the anatomical structure, a textural feature of the at least part of the plurality of pixels representing the anatomical structure, a Gabor filter-based textural feature of the at least part of the plurality of pixels representing the anatomical structure, a Harr-like feature of the at least part of the plurality of pixels representing the anatomical structure, a convolution neural network extracted feature of the at least part of the plurality of pixels representing the anatomical structure, or the like, or any combination thereof. In some embodiments, the gray-level co-occurrence matrix may be represented by the energy related to the image, entropy related to the image, moments of Inertia related to the image, correlation quantity related to the image, or the like, or a combination thereof. The textural feature may be represented by the coarseness of the image, contrast of the image, directionality of the image, line likeness of the image, regularity of the image, roughness of the image.

In some embodiments, the feature information may be used to determine pathological information related to one or more organs (e.g., nodule, tumor, stone). Alternatively or additionally, the feature information may be used to determine density information related to tissues (e.g., the density of fat, the density of air, the density of water). In some embodiments, the feature information may be used to determine specific parts of the one or more organs (e.g., the top of the liver, the bottom of the liver).

In 560, the saving module 450 may save the segmentation result and/or the one or more features into a tag of a digital imaging and communications in medicine (DICOM) file. The tag may correspond to the scanning data. In some embodiment, the tag may include the names of the one or more organs, the locations of the one or more organs, the sizes of the one or more organs, the shapes of the one or more organs, the features of the one or more organs, information related to pixels that belong to which organs, or the like, or any combination thereof. In some embodiments, if the scanning image is a two-dimensional (2D) image, the tag may include layer information. If the scanning image is a three-dimensional (3D) image, the tag may include layer information, volume data information. The layer information may include the name of the one or more organs (e.g., "heart," "liver," "stomach," "lung," "kidney," "spleen," "brain"), the specific parts of the one or more organs (e.g., top of liver, bottom of liver, top of lung, bottom of lung), pathological information related to the one or more organs (e.g., nodule, tumor, stone, cancer), density information related to different tissues (e.g., density of fat, density of air, density of water). The volume data information may include masks representing the one or more organs, meshes representing the one or more organs, sizes (e.g., volumes) of the one or more organs, shapes (e.g., long/short axis ratio information that indicates the degree of being oval) of the one or more organs, specific anatomical position information (also referred to herein as 3D coordinate information) of the one or more organs (e.g., aortic arch, first section of cervical vertebra, caudal vertebra), or the like, or any combination thereof. In some embodiments, the tag may be in the form of tables, graphs, charts, or the like, or any combination thereof.

The saving module 450 may receive the segmentation result and/or the feature(s), and save the segmentation result and/or the feature(s) into a DICOM file. In some embodiments, the saving module 450 may further store the DICOM file on a picture archiving and communication system (PACS) or a local folder for retrieval (e.g., semantic retrieval) or advanced post-processing (e.g., accelerated post-processing). Details regarding the semantic retrieval may be found elsewhere in the present disclosure (e.g., FIG. 8 and the relevant descriptions thereof).

It should be noted that the above description of the process 500 is provided for the purposes of illustration, and is not intended to limit the scope of the present disclosure. For persons having ordinary skills in the art, multiple variations and modifications may be made under the teachings of the present disclosure. However, those variations and modifications do not depart from the scope of the present disclosure. In some embodiments, a pre-processing step may be performed after obtaining the scanning image. For example, the scanning image may be denoised, tailed, zoomed, or a combination thereof.

Figure 6:
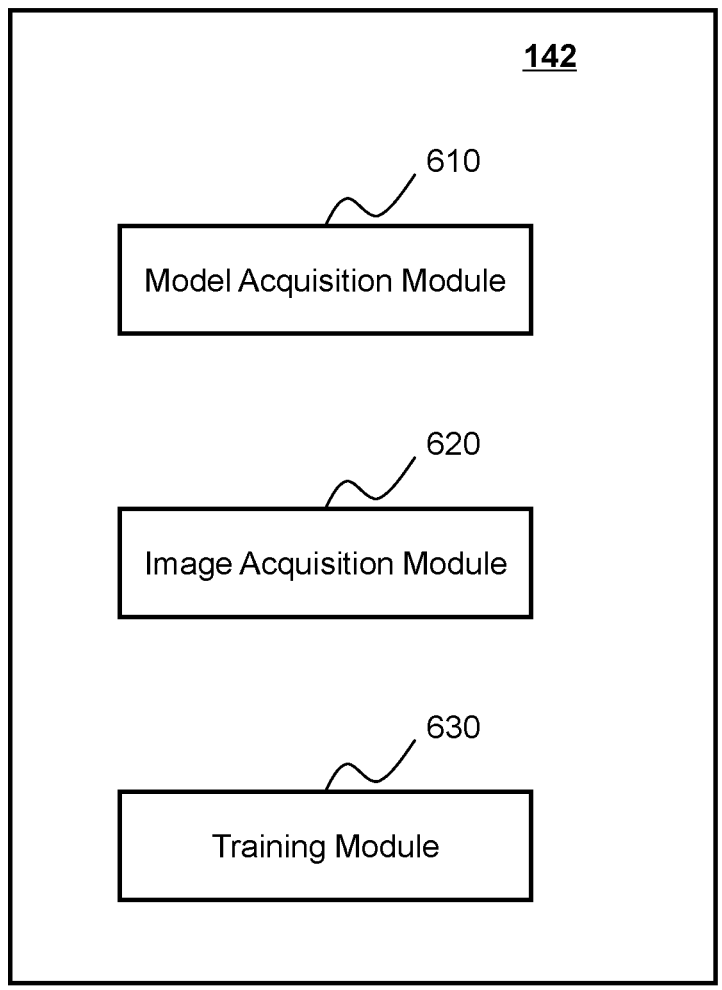
FIG. 6 is a block diagram illustrating an exemplary processing device according to some embodiments of the present disclosure.

FIG. 6 is a block diagram illustrating an exemplary processing device (e.g., the processing engine 142) according to some embodiments of the present disclosure. The processing engine 142 may be implemented on the computing device 200 (e.g., the processor 210) as illustrated in FIG. 2. The processing engine 142 may include a model acquisition module 610, a sample acquisition module 620, and a model training module 630.

The model acquisition module 610 may be configured to obtain a model (e.g., a preliminary segmentation model). In some embodiments, the preliminary segmentation model may include one or more classifiers. Each of the classifiers may have an initial parameter related to the weight of the classifier. The initial parameter related to the weight of the classifier may be adjusted during the training of the preliminary segmentation model. The model acquisition module 610 may obtain the preliminary segmentation model from a storage device (e.g., the storage device 150).

The sample acquisition module 620 may be configured to obtain a plurality of training samples. The plurality of training samples may include a plurality of sample images. The plurality of sample images may be 2D images, 3D images, etc. In some embodiments, each of the plurality of sample images may include an anatomical structure of interest (ASI) represented by a plurality of pixels. The ASI may include one or more particular organs of an anatomical structure. Each of the plurality of pixels may include a pixel value indicating the value of a property of a pixel. Besides, a pixel belonging to an organ may be marked with a name, specifically, the name of the organ. Thus, each of pixels representing the ASI may include a marked name and a pixel value. In some embodiments, the sample acquisition module

620 may obtain the plurality of sample images from a storage device (e.g., the storage device 150) or a database (e.g., PACS, a local folder).

The model training module 630 may be configured to train a model (e.g., the preliminary segmentation model). For example, the model training module 630 may train the preliminary segmentation model to obtain a trained segmentation model using the obtained plurality of training samples (e.g., the sample images). Specifically, the model training module 630 may input the plurality of sample images to the preliminary segmentation model to generate an actual output for the plurality of sample images. Each of the plurality of pixels in the plurality of sample images may include a marked name and a corresponding pixel value. The model training module 630 may determine the pixel values of the plurality of pixels in the plurality of sample images as an input, and determine the marked names (e.g., names of organs) of the plurality of pixels in the plurality of sample images as a desired output. The model training module 630 may compare the actual output with the desired output in a loss function. The loss function may measure the difference between the actual output and the desired output. During the training of the preliminary segmentation model, the model training module 630 may adjust the initial parameters to minimize the loss function. The minimization of the loss function may be iterative. The iteration of minimizing the loss function may be terminated when the value of the newly loss function is less than a predetermined threshold. The predetermined threshold may be set based on various factors, such as the accuracy degree of the model, etc. After minimizing the loss function, the initial parameters of the classifiers in the preliminary segmentation model may be updated, and a trained segmentation model may be generated.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. Two or more of the modules may be combined as a single module. For example, the sample acquisition module 620 may be integrated into the model acquisition module 610 as a single module that may obtain the preliminary segmentation model and the training samples. In some embodiments, the processing engine 142 may include one or more other modules. For example, the processing engine 142 may further include a storage module (not shown in FIG. 6) configured to store the trained segmentation model.

Figure 7:
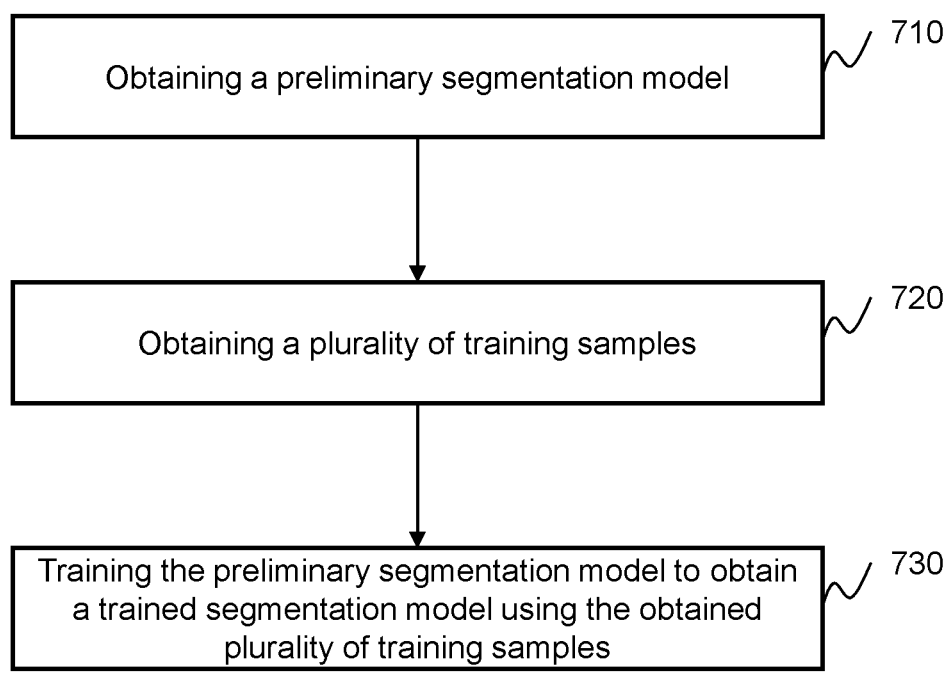
FIG. 7 is a flowchart illustrating an exemplary process for generating a trained segmentation model according to some embodiments of the present disclosure.

FIG. 7 is a flowchart illustrating an exemplary process for generating a trained segmentation model according to some embodiments of the present disclosure. The process 700 may be implemented in the medical imaging system 100 illustrated in FIG. 1. For example, the process 700 may be stored in the storage device 150 and/or the storage 220 in the form of instructions (e.g., an application), and invoked and/or executed by the processing device 140 (e.g., the processor 210 illustrated in FIG. 2, or one or more modules in the processing engine 142 illustrated in FIG. 6). The operations of the illustrated process presented below are intended to be illustrative. In some embodiments, the process 700 may be accomplished with one or more additional operations not described, and/or without one or more of the operations discussed. Additionally, the order in which the operations of the process 700 as illustrated in FIG. 7 and described below is not intended to be limiting.

In 710, the model acquisition module 610 may obtain a preliminary segmentation model. In some embodiments, the preliminary segmentation model may include one or more classifiers. Each of the classifiers may have an initial parameter related to the weight of the classifier. The initial parameter related to the weight of the classifier may be adjusted during the training of the preliminary segmentation model. The model acquisition module 610 may obtain the preliminary segmentation model from a storage device (e.g., the storage device 150).

In some embodiments, exemplary preliminary segmentation models may include a Ranking Support Vector Machine (SVM) model, a decision tree model (e.g., a Gradient Boosting Decision Tree (GBDT) model), a LambdaMART model, an adaptive boosting model, a hidden Markov model, a Hopfield network model, a self-organizing map (SOM), a learning vector quantization (LVQ), a convolutional neural network model (e.g., a multi-scale convolutional neural network model, a super-resolution convolutional neural network model, a denoising convolutional neural network model), a perceptron neural network model, a deep trust network model, a stack self-coding network model, a recurrent neural network model (e.g., a long short term memory (LSTM) neural network model, a hierarchical recurrent neural network model, a bi-direction recurrent neural network model, a second-order recurrent neural network model, a fully recurrent network model, an echo state network model, a multiple timescales recurrent neural network (MTRNN) model), or the like, or any combination thereof.

In 720, the sample acquisition module 620 may obtain a plurality of training samples. The plurality of training samples may include a plurality of sample images. The plurality of sample images may be 2D images, 3D images, etc. In some embodiments, each of the plurality of sample images may include an anatomical structure of interest (ASI) represented by a plurality of pixels. The ASI may be a particular organ of an anatomical structure, such as a heart. Alternatively, the ASI may include more than one particular organ of the anatomical structure, such as a heart, a stomach. Each of the plurality of pixels may include a pixel value indicating the value of a property of a pixel. For example, a pixel value may be or include the luminance value of a pixel, the grey-scale value of a pixel, the color or RGB value of a pixel, the saturation of a pixel, etc. Besides, a pixel belonging to an organ may be marked with a name, specifically, the name of the organ. For example, for a pixel that belongs to a heart, the pixel may be marked with "heart." Thus, each of pixels representing the ASI may include a marked name and a pixel value. In some embodiments, the sample acquisition module 620 may obtain the plurality of sample images from a storage device (e.g., the storage device 150). Alternatively, the sample acquisition module 620 may obtain the plurality of sample images from a database (e.g., PACS, or a local folder).

In 730, the model training module 630 may train the preliminary segmentation model to obtain a trained segmentation model using the obtained plurality of training samples.

The model training module 630 may input the plurality of sample images into the preliminary segmentation mode to generate an actual output for the plurality of sample images. Each of the plurality of pixels representing the ASI in the plurality of sample images may include a marked name and a corresponding pixel value. The model training module 630 may determine the pixel values of the plurality of pixels in the plurality of sample images as an input, and determine the marked names (e.g., the names of organs) of the plurality of pixels in the plurality of samples images as the desired output. The model training module 630 may compare the actual output with the desired output in a loss function. The loss function may measure the difference between the actual output and the desired output. For example, the actual output may correspond to an actual score, and the desired output may correspond to the desired score. In some embodiments, the desired score may be designated as "1," and the actual score may be a probability value between "0" and "1." The loss function may relate to the difference between the actual score and the desired score. The loss function may include but is not limited to a zero-one loss, a perceptron loss, a hinge loss, a log loss, a square loss, an absolute loss, and an exponential loss. During the training of the preliminary segmentation model, the model training module 630 may adjust the initial parameters to minimize the loss function. The minimization of the loss function may be iterative. The iteration of minimizing the loss function may be terminated when the value of the newly loss function is less than a predetermined threshold. The predetermined threshold may be set based on various factors, such as the accuracy degree of the model, etc. After minimizing the loss function, the initial parameters of the classifiers in the preliminary segmentation model may be updated, and a trained segmentation model may be generated.

Figure 8:
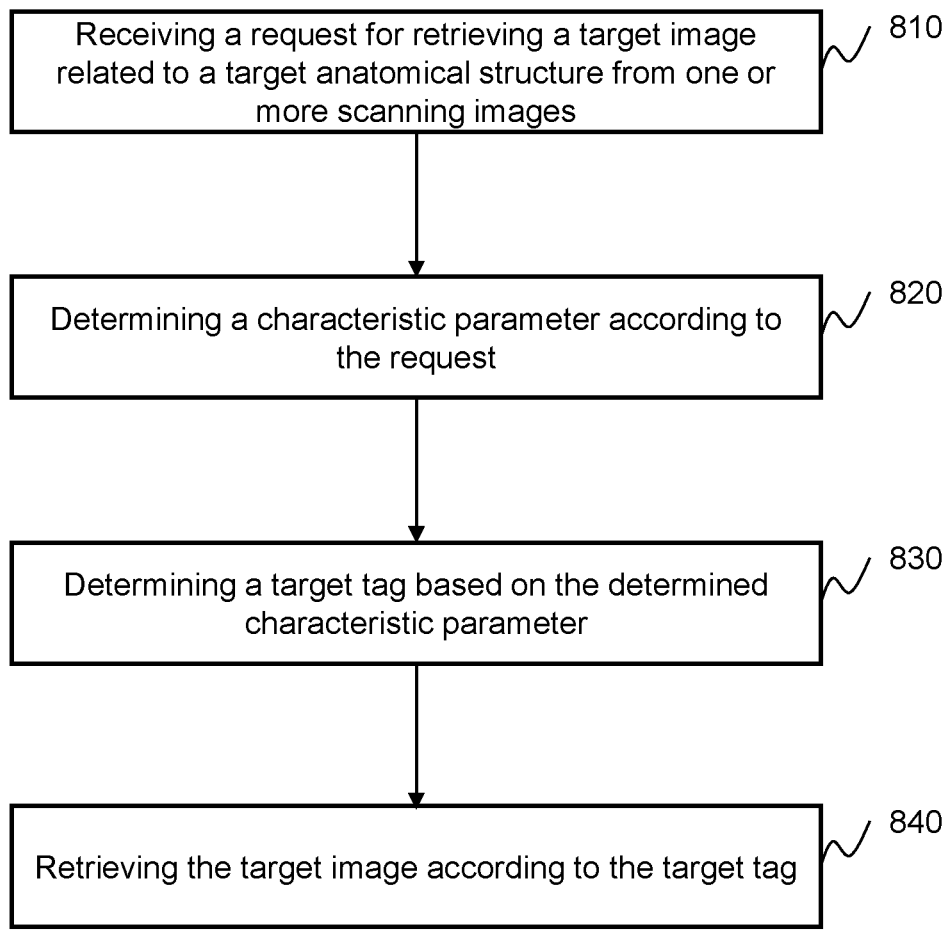
FIG. 8 is a flowchart illustrating an exemplary process for retrieving a target image according to some embodiments of the present disclosure.

FIG. 8 is a flowchart illustrating an exemplary process for retrieving a target image according to some embodiments of the present disclosure. The process 800 may be implemented in the medical imaging system 100 illustrated in FIG. 1. For example, the process 800 may be stored in the storage device 150 and/or the storage 220 in the form of instructions (e.g., an application), and invoked and/or executed by the processing device 140 (e.g., the processor 210 illustrated in FIG. 2, or one or more modules in the processing engine 141 illustrated in FIG. 4). The operations of the illustrated process presented below are intended to be illustrative. In some embodiments, the process 800 may be accomplished with one or more additional operations not described, and/or without one or more of the operations discussed. Additionally, the order in which the operations of the process 800 as illustrated in FIG. 8 and described below is not intended to be limiting.

In 810, the retrieval module 460 may receive a request for retrieving a target image related to a target anatomical structure from one or more scanning images. In some embodiments, the retrieval module 460 may receive the request from a user (e.g., a doctor) via a user interface (e.g., the I/O 230). The request may relate to retrieving a target image containing a target anatomical structure from one or more scanning images. In some embodiments, the target anatomical structure may include one or more target organs. In some embodiments, the one or more scanning images may be stored in a database (e.g., PACS, a local folder). Each of the one or more scanning images may include a tag, including the names of an ASI (e.g., one or more organs), the locations of the ASI (e.g., the one or more organs), the sizes of the ASI (e.g., the one or more organs), the shapes of the ASI (e.g., the one or more organs), the features of the ASI (e.g., the one or more organs), information related to pixels representing the ASI (e.g., the one or more organs), etc. The tag may also include layer information, volume data information, etc.

In 820, the retrieval module 460 may determine a characteristic parameter according to the request. The retrieval module 460 may determine the semantics of the request, and determine the characteristic parameter according to the determined semantics of the request. The semantics may be determined based on a semantics analysis, including a character matching-based word segmentation method (e.g., a maximum matching algorithm, an omni-word segmentation algorithm, a statistical language model algorithm), a sequence annotation-based word segmentation method (e.g., POS tagging), a deep learning-based word segmentation method (e.g., a hidden Markov model algorithm), etc. The characteristic parameter may relate to a characteristic of the target anatomical structure. For example, if the semantics of the request is "splenomegaly," a characteristic parameter of "splenomegaly" may be determined as a size of a spleen, a height of the spleen, etc. As another example, if the semantics of the request is "fatty liver," a characteristic parameter of "fatty liver" may be determined as a gray average of pixels representing a liver. In some embodiments, the characteristic parameter may be determined based on clinical empirical values, or may be default settings of semantics, or may be adjusted by a user (e.g., a doctor).

In 830, the retrieval module 460 may determine a target tag based on the determined characteristic parameter. In some embodiments, the target tag may include the name of the target anatomical structure, the location of the target anatomical structure, the size of the target anatomical structure, the shape of the target anatomical structure, the features of the target anatomical structure, information related to pixels representing the target anatomical structure, etc. For example, for the request with the semantics of "splenomegaly," the target tag may include the name of the target anatomical structure "spleen," information related to the size of the target anatomical structure (e.g., the size larger than a first threshold). As another example, for the request with the semantics of "fatty liver," the target tag may include the name of the target anatomical structure "liver," information related to an average intensity of the pixels representing the liver (e.g., the gray average of the pixels less than a second threshold).

In 840, the retrieval module 460 may retrieve the target image according to the target tag. In some embodiments, the retrieval module 460 may retrieve the target image by traversing the one or more scanning images according to the target tag. For example, for the request with the semantics of "splenomegaly," the retrieval module 460 may select images that contain spleen with a size larger than the first threshold from the one or more scanning images as the target image. As another example, for the request with the semantics of "fatty liver," the retrieval module 460 may select images that contain liver with a gray average of pixels less than the second threshold from the one or more scanning images as the target image. In some embodiments, the retrieval module 460 may transmit the target image to the user (e.g., the doctor) via a user interface (e.g., the I/O 350). For example, the target image may be presented to the user by displaying on a display (e.g., the display 320).

It should be noted that the above description of the process 800 is provided for the purposes of illustration, and is not intended to limit the scope of the present disclosure. For persons having ordinary skills in the art, multiple variations and modifications may be made under the teachings of the present disclosure. However, those variations and modifications do not depart from the scope of the present disclosure. In some embodiments, the one or more scanning images may be used to perform an advanced post-processing (e.g., an advanced segmentation). For example, the retrieval module 460 may retrieve a scanning image from the one or more scanning images. The scanning image may be used to perform an advanced segmentation based on active shape model (ASM), optimal surface detection (OSD), etc.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer-readable media having computer readable program code embodied thereon.

A non-transitory computer readable signal medium may include a propagated data signal with computer readable program code embodied therein, for example, in baseband or as part of a carrier wave. Such a propagated signal may take any of a variety of forms, including electromagnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object-oriented programming language such as Java, Scala, Smalltalk, Eiffel, JADE, Emerald, C++, C #, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software-only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed object matter requires more features than are expressly recited in each claim. Rather, inventive embodiments lie in less than all features of a single foregoing disclosed embodiment.

In some embodiments, the numbers expressing quantities, properties, and so forth, used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A system, comprising:
    at least one storage device storing a set of instructions; and
    at least one processor in communication with the at least one storage device, wherein when executing the set of instructions, the at least one processor is configured to cause the system to:
        obtain a scanning image, the scanning image including a plurality of pixels representing an anatomical structure;
        obtain a trained segmentation model;
        determine a location probability distribution of the anatomical structure in the scanning image based on the trained segmentation model;
        generate a segmentation result related to the anatomical structure based on the location probability distribution;
        extract one or more features related to the anatomical structure based on the segmentation result; and
        save the one or more features into a tag of a digital imaging and communications in medicine (DICOM) file, the tag corresponding to the scanning image.

2. The system of claim 1, wherein:
    the system includes a display; and
    the at least one processor is further configured to cause the system to:
        generate a marked image based on the segmentation result related to the anatomical structure; and
        display, by the display, the marked image to a user.

3. The system of claim 1, wherein the segmentation result is represented by a contour of the anatomical structure.

4. The system of claim 1, wherein the segmentation result includes at least part of the plurality of pixels representing the anatomical structure, and
    the one or more features related to the anatomical structures include at least one of:
        an average intensity of the at least part of the plurality of pixels representing the anatomical structure;
        an entropy of the at least part of the plurality of pixels representing the anatomical structure;
        a homogeneous degree of the at least part of the plurality of pixels representing the anatomical structure;
        a gray-level co-occurrence matrix of the at least part of the plurality of pixels representing the anatomical structure;
        a Harr-like feature of the at least part of the plurality of pixels representing the anatomical structure; or
        a convolution neural network extracted feature of the at least part of the plurality of pixels representing the anatomical structure.

5. The system of claim 1, wherein the trained segmentation model is generated according to a process for training a segmentation model, the process comprising:
    obtaining a preliminary segmentation model;
    obtaining a plurality of training samples; and
    training the preliminary segmentation model to obtain the trained segmentation model according to the obtained plurality of training samples.

6. The system of claim 1, wherein the trained segmentation model is a decision tree model or a neural network model.

7. A system, comprising:
    at least one storage device storing a set of instructions; and
    at least one processor in communication with the at least one storage device, wherein when executing the set of instructions, the at least one processor is configured to cause the system to:
        receive a request for retrieving a target image related to a target anatomical structure from a database containing one or more scanning images;
        determine a characteristic parameter according to the request;
        determine a target tag based on the determined characteristic parameter; and
        retrieve the target image from the database according to the target tag, wherein the one or more scanning images are processed according to a process for processing an image, the process comprising:
            obtaining a scanning image, the scanning image including a plurality of pixels representing an anatomical structure;
            obtaining a trained segmentation model;
            determining a location probability distribution of the anatomical structure in the scanning image based on the trained segmentation model;
            generating a segmentation result related to the anatomical structure based on the location probability distribution;
            extracting one or more features related to the anatomical structure based on the segmentation result; and
            saving the one or more features into a tag of a DICOM file into the database, the tag corresponding to the scanning image.

8. The system of claim 7, wherein to determine a characteristic parameter according to the request, the at least one processor is configured to cause the system to:
    determine semantics of the request; and
    determine the characteristic parameter according to the determined semantics of the request.

9. The system of claim 7, wherein the at least one processor is further configured to cause the system to:
    retrieve the scanning image; and
    perform an advanced segmentation on the scanning image based on at least one of Active Shape Model or Optimal Surface Detection.

10. A method implemented on a computing device having at least one processor and at least one storage device, the method comprising:
    obtaining a scanning image, the scanning image including a plurality of pixels representing an anatomical structure;
    obtaining a trained segmentation model;
    determining a location probability distribution of the anatomical structure in the scanning image based on the trained segmentation model;

generating a segmentation result related to the anatomical structure based on the location probability distribution;

extracting one or more features related to the anatomical structure based on the segmentation result; and saving the one or more features into a tag of a DICOM file, the tag corresponding to the scanning image.

11. The method of claim 10, wherein the method further comprises:

generating a marked image based on the segmentation result related to the anatomical structure; and displaying the marked image to a user.

12. The method of claim 10, wherein the segmentation result is represented by a contour of the anatomical structure.

13. The method of claim 10, wherein the segmentation result is represented as a mesh.

14. The method of claim 10, wherein:

the segmentation result includes at least part of the plurality of pixels representing the anatomical structure; and the one or more features related to the anatomical structures include at least one of:

an average intensity of the at least part of the plurality of pixels representing the anatomical structure;

an entropy of the at least part of the plurality of pixels representing the anatomical structure;

a homogeneous degree of the at least part of the plurality of pixels representing the anatomical structure;

a gray-level co-occurrence matrix of the at least part of the plurality of pixels representing the anatomical structure;

a Harr-like feature of the at least part of the plurality of pixels representing the anatomical structure; or a convolution neural network extracted feature of the at least part of the plurality of pixels representing the anatomical structure.

15. The method of claim 10, wherein the trained segmentation model is generated according to a process for training a segmentation model, the process comprising:

obtaining a preliminary segmentation model;

obtaining a plurality of training samples; and training the preliminary segmentation model to obtain the trained segmentation model according to the obtained plurality of training samples.

16. The method of claim 10, wherein the trained segmentation model is a decision tree model or a neural network model.

17. The system of claim 1, wherein the segmentation result is represented by a mask.

18. The system of claim 1, wherein the tag includes layer information and volume data information.

19. The method of claim 10, wherein the segmentation result is represented by a mask.

* * * * *